(12) United States Patent
Chiku

(10) Patent No.: US 7,935,541 B2
(45) Date of Patent: May 3, 2011

(54) IMMUNOCHROMATOGRAPHY METHOD USING FRAGMENTED ANTIBODY

(75) Inventor: Hiroyuki Chiku, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 229 days.

(21) Appl. No.: 12/239,640

(22) Filed: Sep. 26, 2008

(65) Prior Publication Data

US 2009/0087927 A1    Apr. 2, 2009

(30) Foreign Application Priority Data

Sep. 28, 2007  (JP) .................................. 2007-254173
Feb. 12, 2008  (JP) .................................. 2008-029988

(51) Int. Cl.
*G01N 33/553* (2006.01)

(52) U.S. Cl. ........ 436/530; 435/7.1; 435/7.94; 435/962; 436/525; 436/177; 436/178; 436/170; 436/541; 436/826

(58) Field of Classification Search .................... 435/7.1, 435/7.94, 962; 436/525, 177, 178, 170, 541, 436/826
See application file for complete search history.

(56) References Cited

U.S. PATENT DOCUMENTS

| | | | | |
|---|---|---|---|---|
| 5,441,896 A | * | 8/1995 | Noppe et al. | ................... 436/525 |
| 5,607,863 A | * | 3/1997 | Chandler | ...................... 436/518 |

FOREIGN PATENT DOCUMENTS

| | | | |
|---|---|---|---|
| JP | 7-83923 A | 3/1995 |
| JP | 7-146280 A | 6/1995 |
| JP | 11-295313 A | 10/1999 |
| JP | 2002-202307 A | 7/2002 |
| JP | 2005-512074 A | 4/2005 |
| WO | WO-03/050292 A2 | 6/2003 |

* cited by examiner

*Primary Examiner* — Bao-Thuy L Nguyen
(74) *Attorney, Agent, or Firm* — Birch, Stewart, Kolasch & Birch, LLP

(57) ABSTRACT

An object of the present invention is to overcome the problem of nonspecific adsorption of a labeled antibody on the detection site and to provide an immunochromatography method by which the false positive signal can be suppressed, and wherein the detection sensitivity is high and the highly reliable measurement can be performed. The present invention provides an immunochromatography method, which comprises developing an analyte and a labeling substance modified with a first antibody against the analyte on a porous carrier in a state where the analyte and the labeling substance is mixed, and capturing the analyte and the labeling substance at the reaction site on the porous carrier having a second antibody against the analyte, so as to detect the analyte; wherein a fragmented antibody is used as the first antibody and/or the second antibody; an analyte is detected via amplification using an amplification solution which contains a compound containing silver and a reducing agent for silver ions; and the ratio of the non-specifically adsorbed labeling substance in the pre-amplification detection site and the non-detection site of the porous carrier is between 0.4 to 2.5 in a system where the density of the non-specifically adsorbed labeling substance is $10^6$/mm2 or less.

5 Claims, 3 Drawing Sheets

C.E: Comparive Example

IMMUNOCHROMATOGRAPHY METHOD USING FRAGMENTED ANTIBODY

TECHNICAL FIELD

The present invention relates to an immunochromatography method using a labeled antibody.

BACKGROUND ART

Immunoassays are widely used as methods for qualitatively or quantitatively measuring the presence of an analyte existing in a biological sample such as urine or blood. Of these immunoassays, an immunochromatography method is generally used with high frequency since its implementation is simple and enables short-time measurement.

The competitive reaction and the sandwich reaction are broadly used as immunoreactions to be employed in immunochromatography methods. In particular, the sandwich reaction is mainly employed for an immunochromatography method. In a typical example of the use of the sandwich reaction, the following procedures are performed to detect an analyte comprising an antigen in a sample. (1) A chromatographic medium having a reaction site is prepared by immobilizing a fine particle as a solid phase fine particle that has been sensitized with an antibody against an antigen that is an analyte on a chromatographic medium or by directly immobilizing the antibody on a chromatographic medium. (2) Meanwhile, a labeled antibody is prepared by sensitizing a labeled substance with an antibody capable of specifically binding to an analyte. (3) The labeled antibody is caused to migrate chromatographically on a chromatographic medium together with a sample.

The thus immobilized antibody is as an immobilized reagent at the detection site formed on the chromatographic medium by the above procedures. The labeled antibody specifically binds to the reagent via an antigen that is an analyte. As a result, the presence, absence, or the amount of an analyte in a sample is measured by visually determining the presence, absence, or the degree of signals generated when the labeled antibody is captured at the detection site.

When substances which act in ultratrace amounts (including bioactive substances or environmental pollutants such as toxins, hormones, or agricultural chemicals) are detected, the detection signal may sometimes be amplified. For example, when an enzyme such as alkaline phosphatase or peroxidase may be used as a labeling substance, an enzyme-linked coloring method can be used for signal amplification. When gold colloid is used as a labeling substance, silver amplification method can be used for signal amplification.

When signal amplification is generally carried out in immunochromatography method or the like, not only signal from labeling substance which was specifically bound to a solid phase but also signal from labeling substance which was non-specifically adsorbed are amplified. Therefore, suppression of non-specific adsorption is important object. For such purpose, after an antibody is immobilized, the solid phase is blocked with a non-specifically adsorption suppressing agent such as protein (for example, albumin, globulin, or casein) or polymer (for example, polyvinyl alcohol, or polyvinylpyrrolidone).

Patent document 1 JP Patent Publication (Kokai) No. 7-146280 A (1995)
Patent document 2 JP Patent Publication (Kokai) No. 11-295313 A (1999)
Patent document 3 JP Patent Publication (Kohyo) No. 2005-512074 A
Patent document 4 JP Patent Publication (Kokai) No. 2002-202307 A
Patent document 5 JP Patent Publication (Kokai) No. 7-83923 A (1995)

DISCLOSURE OF THE INVENTION

However, the aforementioned conventional blocking method is not sufficient for suppressing non-specific adsorption. As a result that a labeling substance is non-specifically adsorbed on the detection site, false positive result may be obtained. Therefore, it is desired to develop a technique which can reduce non-specific adsorption of a labeling substance onto the detection site.

An object to be achieved by the present invention is to overcome the problem of nonspecific adsorption of a labeled antibody on the detection site, and to provide an immunochromatography method by which the false positive signal can be suppressed, and wherein the detection sensitivity is high and the highly reliable measurement can be performed.

The present invention provides an immunochromatography method, which comprises developing an analyte and a labeling substance which is modified with a first binding substance against the analyte in a mixed state on a porous carrier and capturing the analyte and the label at a reaction site on the porous carrier having a second binding substance against the analyte or a substance capable of binding to the first binding substance against the analyte, so as to detect the analyte; wherein
a fragmented antibody is used as the first antibody and/or the second antibody;
an analyte is detected via amplification using an amplification solution which contains a compound containing silver and a reducing agent for silver ions;
the density of the non-specifically adsorbed labeling substance is $10^6/mm^2$ or less (preferably $10^5/mm^2$ or less); and the ratio of the number of the non-specifically adsorbed labeling substance in the pre-amplification detection site and that in the non-detection site of the porous carrier is between 0.4 to 2.5 (preferably 0.7 to 2.0, and more preferably 0.8 to 1.5)

Preferably, a fragmented antibody is used as the binding substance; the density of "the second binding substance against the analyte, or the substance capable of binding to the first binding substance against the analyte" at the detection site is 0.007 $\mu g/mm^2$ to 1.1 $\mu g/mm^2$, and the particle diameter of the labeling substance is 20 nm to 80 nm.

More preferably, a fragmented antibody is used as the binding substance; the density of "the second binding substance against the analyte, or the substance capable of binding to the first binding substance against the analyte" at the detection site is 0.014 $\mu g/mm^2$ to 0.84 $\mu g/mm^2$ and the particle diameter of the labeling substance is 20 nm to 80 nm.

Further more preferably, a fragmented antibody is used as the binding substance; the density of "the second binding substance against the analyte, or the substance capable of binding to the first binding substance against the analyte" at the detection site is 0.021 $\mu g/mm^2$ to 0.63 $\mu g/mm^2$, and the particle diameter of the labeling substance is 20 nm to 80 nm.

Preferably, the first binding substance is an antibody, and/or the second binding substance is an antibody.

Preferably, a fragmented antibody which is an Fab fragment and/or F(ab')$_2$ fragment and/or Fab' fragment is used as the first binding substance only.

Preferably, the porous carrier is nitrocellulose or polyethylene.

According to the present invention, a false positive result can be suppressed, and high sensitive and clear assay result can be obtained in an immunochromatography method.

PREFERRED EMBODIMENT OF THE INVENTION

The analyte in the present invention is not particularly limited, so long as it can bind to an antibody via immunochemical reaction (antigen-antibody reaction in the present invention) and form a sandwich immune complex. Examples thereof include virus (for example, influenza virus, adenovirus, RSV, HIV, HBV, and HCV); microorganisms such as bacterial (for example, pathogenic bacteria such as *E. coli* O157 and Methicillin-resistant *Staphylococcus aureus* (MRSA)), streptomycete, yeast, or mold, and antibody against these microorganisms; toxin which is produced by bacteria or the like; or an antigenic peptide in biological sample such as tumor marker antigen.

The type of the test sample that contains the analyte is not particularly limited, as long as it may comprise an analyte. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

In the immunochromatography of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

Figure 1:
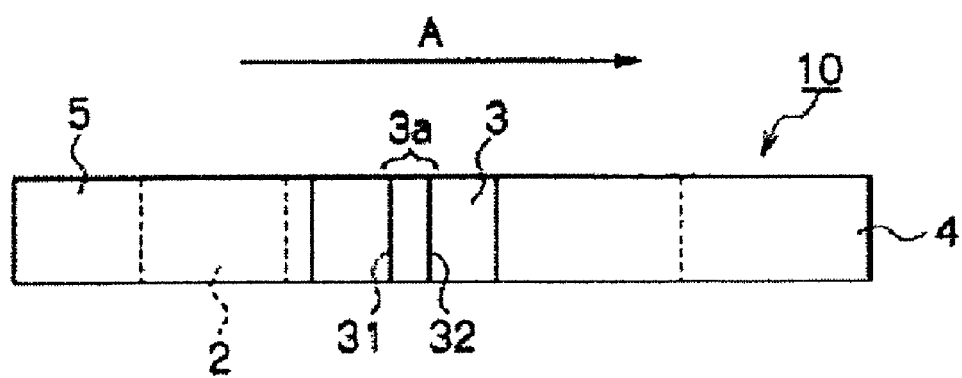
FIG. 1 is a plain view schematically illustrating one embodiment of an immunochromatography kit that can be used in the present invention.
Figure 2:
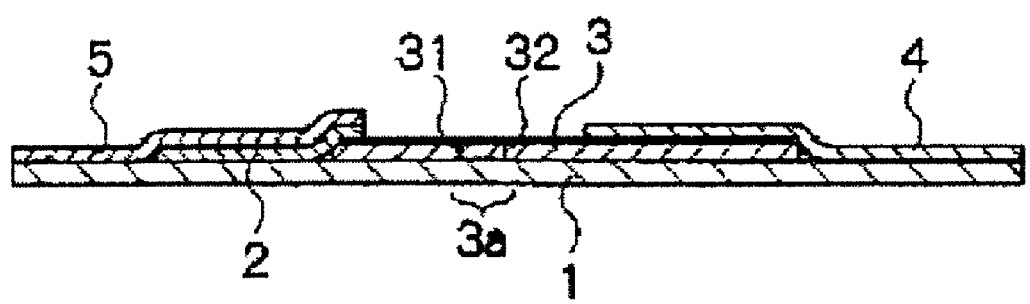
FIG. 2 is a longitudinal sectional view schematically illustrating a longitudinal sectional view of the immunochromatography kit shown in FIG. 1.

The type of an immunochromatographic strip that can be used in the immunochromatography of the present invention is not particularly limited, as long as it is an immunochromatographic strip that can be used in a common immunochromatography. The width and shape of the strip are not particularly limited so long as the strip is easy to operate. For example, FIG. 1 schematically shows a longitudinal section of one example of the immunochromatographic strip of the present invention. FIG. 2 is a longitudinal sectional view schematically illustrating a longitudinal sectional view of the immunochromatography kit shown in FIG. 1.

In an immunochromatographic strip 10 of the present invention, a sample-adding pad 5, a labeling substance-retaining pad (e.g. a gold colloid antibody-retaining pad) 2, a chromatographic carrier (e.g. an antibody-immobilized membrane) 3, and an absorbent pad 4 are disposed in this order on an adhesive sheet 5 from the upstream to the downstream of a development direction (direction represented by (A) in FIG. 1)

The chromatographic carrier 3 has a capture site 3a which is composed of a detection site 31, and if desired a control site 32 that is a region on which a control antibody or antigen is immobilized.

The detection site in the present invention is a site which is prepared by immobilizing a detecting substance (namely, an antibody which specifically binds to an analyte) on a part of a porous carrier. The detecting substance may be directly immobilized on a part of porous carrier via a physical or chemical bond. Alternatively, the detecting substance may be bound physically or chemically to fine particles such as latex particles, and thereafter, the fine particles are immobilized on a part of the porous carrier by trapping them thereon. It is also possible that two or more types of the detecting substances are immobilized on a single carrier.

The detection site can be prepared by coating or dotting a detecting substance. The density of the detecting substance at the detection site can be determined by the coating concentration and coating amount of the detecting substance.

For example, when a nitrocellulose strip having a width of 5 mm is coated with an antibody to form a coated line having a width of 1 mm, the density of the antibody to be immobilized in a detection zone is as follows. Specifically, when the strip is coated with an antibody having a concentration of 0.1 mg/mL at 0.7 µL/cm, the density is 0.007 µg/mm$^2$. When the strip is coated with an antibody having a concentration of 1.0 mg/mL at 0.7 µL/cm, the density is 0.07 µg/mm$^2$. When the strip is coated with an antibody having a concentration of 10.0 mg/mL at 0.7 µL/cm, the density is 0.7 µg/mm$^2$. Further, when a coated line having a width of 2 mm is formed, the density of the antibody is as follows. Specifically, when the strip is coated with an antibody having a concentration of 0.1 mg/mL at 2.1 µL/cm, the density is 0.011 µg/mm$^2$. When the strip is coated with an antibody having a concentration of 1.0 mg/mL at 2.1 µL/cm, the density is 0.11 µg/mm$^2$. When the strip is coated with an antibody having a concentration of 10.0 mg/mL at 2.1 µL/cm, the density is 1.1 µg/mm$^2$.

Further, when polyethylene strip is used, an antibody cannot be immobilized only by coating and drying the antibody, which is different from the case of using nitrocellulose. The antibody may be adsorbed on latex microsphere and is then spotted and dried, so that the antibody can be immobilized on a strip.

When an antibody is immobilized on polyethylene piece (AQ800, 1 cm×5 cm×0.1 cm; ASAHI KASEI CHEMICAL), the following procedure is used. An antibody is immobilized on latex microsphere (Bangs Laboratories Inc.) having a particle size of 0.3 µm by the method described in Adsorption to Microspheres (TechNote 204, Bangs Laboratories Inc.) to prepare an antibody immobilized latex microsphere. The antibody immobilized latex microsphere is spotted on polyethylene piece, the spot is spread circularly. By drying it at 37° C. for 30 minutes, latex microspheres can be immobilized. Depending on the particle diameter of latex microspheres used here, the amount of antibody which can be immobilized per 1 particle varies. Depending on the particle concentration and spotting amount, the density of particle at the time of spotting varies. Therefore, by changing these parameters, the density of immobilized antibody can be controlled in the case of polyethylene strip.

For example, 47.6 μg of antibody can be immobilized on 1 mg of particle of latex microsphere having a particle size of 0.3 μm (TechNote 204, Bangs Laboratories Inc.). This antibody immobilized latex microsphere is adjusted to 1% (=0.01 mg/μl), and 3 μl of it is spotted on polyethylene piece (AQ800, 1 cm×5 cm×0.1 cm; ASAHI KASEI CHEMICAL), and then it is spread into a circle having a diameter of 5 mm. The antibody density of the detection site is 0.073 μg/mm$^2$. Similarly, the antibody immobilized latex microsphere having a particle size of 0.3 μm is adjusted to 1.5% (=0.015 mg/μl), and 3 μl of it is spotted on polyethylene piece (AQ800, 1 cm×5 cm×0.1 cm), and then it is spread into a circle having a diameter of 5 mm. The antibody density of the detection site is 0.11 μg/mm$^2$.

The non-detection site on the porous carrier in the present invention means a site where detection is not carried on the porous carrier. Namely, it means a region other than "the detection site" and "the control site". In the present invention, the number of the non-specifically adsorbed labeling substance is compared between "the detection site" and "the non-detection site on the porous carrier". Therefore, it is preferred that "the non-detection site on the porous carrier" is close to "the detection site". For example, "the non-detection site on the porous carrier" is places between "the detection site" and the control site on a strip.

"The number of the non-specifically adsorbed labeling substance" in the present invention means the number of the labeling substance which is remaining on the porous carrier after a sample solution containing no antigen is dotted and developed on an immunochromatography kit and it is washed (before amplification). Specific method of measurement is mentioned below. 100 μL of PBS buffer containing 1% BSA is dotted to the influenza immunochromatography kit, and is developed for 15 minutes. The water absorption pad is removed, and a new water absorption pad (cellulose membrane cut to the size of 5 mm×100 mm) is adhered at the same place. Then, the strip is placed in a microtube containing 700 μL of PBS buffer containing 1% BSA in such a way that a sample addition site is immersed in a solution, and is allowed to stand for 1 hour, so as to wash the membrane. Subsequently, the strip is removed from the tube, and pads are removed. Then, a portion containing "detection site (line portion) of 2.0 mm width (line portion is 1 mm width, and the upstream (0.5 mm) and the downstream (0.5 mm) are contained), and "non-detection site on porous carrier (non-line portion)" (intermediate site between "line portion" and control site) of 2.0 mm width, are cut out. The amount of gold at each site is quantified by HR-ICP-MS. Gold is used as the labeling substance. The density of non-specifically adsorbed labeling substance at only "detection site" was calculated from the density of non-specifically adsorbed labeling substance at "non-detention site on the porous carrier".

In the present invention, it was found that the ratio (L/BG) of the number of non-specifically adsorbed labeling substance on detection site (L) to the number of non-specifically adsorbed labeling substance on the non-detection site on the porous carrier (BG) is important. If L/BG is more than 2.5, false positive signal may occur, since the ratio of the labeling substance non-specifically adsorbed on the detection site as compared with the non-detection site is increased. Further the detection sensitivity is too low even without false positive signal, since the amplification time becomes too short. In the present invention, "the false positive" is defined as the case where "the time for detection of line after a sample solution containing no antigen is dotted, developed and washed, followed by amplification" is within 30 seconds. As in the case where L/BG" is less than 0.4, when the amount of nonspecifically adsorbed labeling substance on the detection site is too smaller than that on the non-detection site, the absolute amount of the labeling substance which is specifically trapped by the antigen-antibody reaction is small. Therefore, there is a problem that signal becomes weak and the sensitivity is decreased.

Namely, in the present invention, the value of L/BG is 0.4 to 2.5, preferably 0.7 to 2.0, and more preferably 0.8 to 1.5.

One reason why labeled antibody is non-specifically adsorbed on the detection site in the immunochromatography is that, if Fc region of the antibody is exposed on the surface when the antibody is adsorbed on the labeled particle, then this Fe region is non-specifically adsorbed to the antibody of the detection site. Therefore, a fragmented antibody is preferably used as the first binding substance, and more preferably a fragmented antibody which is an Fab fragment and/or F(ab')$_2$ fragment and/or Fab' fragment is used as the first binding substance only. Thus, non-specific adsorption on the detection site can be suppressed.

In the present invention, a labeling substance is modified with a first binding substance reacting with the test substance. The type of the first binding substance reacting with the test substance may be any substance so long as it has an affinity against the test substance. Examples of the first binding substance may include an antibody against the test substance (antigen), an antigen against the test substance (antibody), or an aptamer against the test substance (protein, low molecular weight compound, or the like), but are not limited thereto.

In the present invention, the porous carrier has (a) a second binding substance reacting with the test substance, or (b) a substance binding with the first binding substance. The type of the second binding substance reacting with the test substance may be any substance so long as it has an affinity against the test substance. Examples of the second binding substance may include an antibody against the test substance (antigen), an antigen against the test substance (antibody), or an aptamer against the test substance (protein, low molecular weight compound, or the like), but are not limited thereto. The second binding substance may be the same as or different from the first binding substance. Examples of the substance binding with the first binding substance may be the test substance, or a substance having a site which is recognized by the first binding substance, and may be a substance which is obtained by binding a derivative of the test substance with a protein (for example, BSA).

Preferably, the first binding substance is an antibody, and/or the second binding substance is an antibody.

An antibody comprises two heavy chains and two light chains and has a Y-shaped quadruplex structure as a basic structure. These heavy and light chains are linked via disulfide bonds so as to form heterodimers. Furthermore, the heterodimers are linked via two disulfide bonds, so as to form a Y-shaped heterotetramer. A V-shaped portion corresponding to the upper half of the Y shape is referred to as "Fab fragment," comprising two light chains and two heavy chains. An antibody binds to an antigen at the tip portions of the two Fab fragments. Moreover, the lower half linear portion of the Y shape is referred to as "Fc fragment," comprising two heavy chains. The fragmented antibody used in the present invention can be prepared by removing Fc fragment from untreated antibody by enzyme or chemical treatment or using genetic engineering techniques.

Representative methods for preparation of fragmented antibodies are the following two methods. First, when an antibody is treated with a papain enzyme, the antibody is denatured into two Fab fragments and one Fc fragment. Furthermore, when an antibody is treated with a pepsin enzyme, the antibody is denatured into $F(ab')_2$ in which two Fab fragments are linked and an Fc fragment. Furthermore, $F(ab')_2$ can also be converted into Fab' via treatment with a reducing agent such as 2-mercaptoethylamine. Examples of an enzyme for preparation of a fragmented antibody include, other than the above enzymes, ficin, lysyl endopeptidase, V8 protease, bromelin, clostripain, metalloendopeptidase, and activated papain prepared by activation of papain. Fab fragments, $F(ab')_2$ fragments, and Fab' fragments obtained by treatment with such enzyme contain antibody binding sites, however, unnecessary Fc fragments have been removed from the enzyme. Therefore, the use of these fragments in antigen detection results in decreased nonspecific adsorption and decreased noise. The fragmented antibody used in the present invention is not limited to those prepared by the aforementioned method, and may include any antibody from which Fc fragment is removed.

In the present invention, a fragmented antibody can be used regardless of animal species, subclasses, and the like. Examples of antibodies that can be used in the present invention include mouse IgG, mouse IgM, rat IgG, rat IgM, rabbit IgG, rabbit IgM, goat IgG, goat IgM, sheep IgG, and sheep IgM. They can be used as either polyclonal or monoclonal antibodies.

Examples of a material for the labeling substance-retaining pad is prepared by preparing a suspension containing a labeling substance having a detecting substance immobilized thereon and coating the suspension on the pad (for example, a cellulose filter paper, glass fibers, and a nonwoven fabric) and then drying it.

As a labeling substance used in detection, a color particle used in immune agglutination can be used. For example, metals such as a metal colloid can be used. Liposomes or microcapsules containing pigments can also be used as such color particles. Conventionally known color metal colloids can all be used as such color particles for labeling. Examples of such color metal colloids include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. Such a metal colloid can be bound to a specifically binding substance according to conventionally known methods (e.g. The Journal of Histochemistry and Cytochemistry, Vol. 30, No. 7, pp. 691-696 (1982)). That is to say, a metal colloid is mixed with a specifically binding substance (e.g. an antibody) in a suitable buffer at room temperature for 5 or more minutes. After completion of the reaction, a precipitate obtained by centrifugation is dispersed in a solution containing a dispersant such as polyethylene glycol to obtain a metal colloid-labeled specifically binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.).

According to the present invention, in an immunochromatography using, as a labeling substance used in detection, a metal colloid labeling substance, a metallic sulfide labeling substance, a metal alloy labeling substance (hereinafter also referred to as a metallic labeling substance), or a metal-containing polymer particle labeling substance, the signal from the aforementioned metallic labeling substance can be amplified. Specifically, after formation of a complex of the analytical target and the labeling substance used in detection, silver ions supplied from a compound containing silver such as an inorganic silver salt or an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target. Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal.

In the immunochromatography of the present invention, a metal colloid labeling substance or a metallic sulfide labeling substance may be used as a labeling substance for labeling an antibody or antigen which specifically binds to an analytical target (an antigen or an antibody), or for labeling a standard compound. The type of such a metal colloid labeling substance or a metallic sulfide labeling substance is not particularly limited, as long as it can be used in an ordinary immunochromatography. Examples of such a metal colloid labeling substance include a platinum colloid, a gold colloid, a palladium colloid, a silver colloid, and a mixture thereof. Examples of such a metallic sulfide labeling substance include sulfides of iron, silver, palladium, lead, copper, cadmium, bismuth, antimony, tin, and mercury. In the immunochromatography of the present invention, one or more selected from these metal colloid labeling substances and/or metallic sulfide labeling substances may be used as a labeling substances).

In the immunochromatography of the present invention, if the particle diameter of a labeling substance is less than 20 nm, non-specific adsorption tends to increase slightly. If the particle diameter of a labeling substance is more than 80 nm, signal per single particle is increased but the particle is likely to be agglutinated, and as a result the detection sensitivity tends to be decreased slightly. Therefore, the particle diameter of the labeling substance is preferably between 20 nm and 8 on.

As to the detection site, as the density of the detecting substance is increased, the signal tends to be increased. If the density of the detecting substance is decreased, the signal tends to be decreased. If the density is less than 0.007 $\mu g/mm^2$, the detection sensitivity tends to be decreased slightly. If the density is more than 1.1 $\mu g/mm^2$, the non-specific adsorption amount tends to be increased slightly, and as a result the detection sensitivity tends to be decreased slightly. Therefore, the density of the detecting substance at the detection site is preferably between 0.007 $\mu g/mm^2$ and 1.1 $\mu g/mm^2$, and more preferably between 0.014 $\mu g/mm^2$ and 0.84 $\mu g/mm^2$, and further more preferably between 0.021 $\mu g/mm^2$ and 0.63 $\mu g/mm^2$.

The porous carrier used in the present invention may include a nitrocellulose membrane, a polyethylene membrane, a cellulose membrane, an acetyl cellulose membrane, a polysulfone membrane, a polyether sulfone membrane, a nylon membrane, glass fibers, a nonwoven fabric, a cloth, threads or the like. For the purpose of preparing an immunochromatography kit with suppressed non-specific adsorption and high detection sensitivity, it is preferred to use a nitrocellulose membrane or a polyethylene membrane.

Preferably, after immobilization of a detecting substance, the porous carrier is subjected to non-specific adsorption suppressing treatment such as a treatment with an inactive protein, and is used.

As described in JP Patent Publication (Kokai) No. 2006-189317A, it is known that non-specific adsorption reaction is decreased at a detection site which was formed with a detecting substance and a non-specific adsorption suppressing agent. Such non-specific adsorption suppressing agent is preferably used in the present invention, since non-specific adsorption reaction can be further suppressed. Examples of the non-specific adsorption suppressing agent which can be used in the present invention may include at least one of albumin, casein, globulin, gelatin, skim milk, polyvinyl alcohol, polyvinylpyrrolidone, and polyethylene glycol. As a specific example, at the time of preparing a detection site, an antibody and a casein may be mixed and coated as a line-shape.

Further, a detection site may preferably be prepared with a detecting substance and at least one of the stabilizers as described in JP Patent Publication (Kokai) No. 2001-289851A (for example, arginine, lysine, histidine, ornithine, citrulline, and glucosamine), since non-specific adsorption can be further suppressed. As a specific example, at the time of preparing a detection site, an antibody and a arginine may be mixed and coated as a line-shape.

Further, the density of the labeling substance which is trapped at the detection site when an antigen is detected at an antigen concentration which is $1/100$ of the antigen concentration which immunochromatography kit before amplification can detect, is approximately $10^5/mm^2$. Therefore, in order to detect it, the density of non-specifically adsorbed labeling substance is $10^5/mm^2$ or less. Therefore, in the immunochromatography of the present invention, the density of non-specifically adsorbed labeling substance is $10^6/mm^2$ or less, and preferably $10^5/mm^2$ or less.

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing unspecific adsorption before use.

The absorbent pad is a portion for physically absorbing the added sample as a result of the chromatographic migration and for absorbing and removing an unreacted labeling substance, etc. that is not immobilized on the detection portion of the chromatographic carrier. Examples of a material for the absorbent pad include water-absorbing materials such as a cellulose filter paper, a nonwoven fabric, a cloth or cellulose acetate. The chromatographic speed after the chromatographic leading end of the added sample has reached the absorbing portion varies depending on the material and size of the absorbent material, etc. Thus, a speed adequate for the measurement of the analytical target can be determined by selection of the material and size of the absorbent material.

According to the present invention, in an immunochromatography using, as a labeling substance used in detection, a metal colloid labeling substance, a metallic sulfide labeling substance, a metal alloy labeling substance (hereinafter also referred to as a metallic labeling substance), or a metal-containing polymer particle labeling substance, the signal from the aforementioned metallic labeling substance can be amplified. Specifically, after formation of a complex of the analytical target and the labeling substance used in detection, silver ions supplied from a compound containing silver such as an inorganic silver salt or an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target. Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal.

The apparatus used to perform such an immunochromatography in the present invention may comprise a compound containing silver and a reducing agent for silver ion. A signal is amplified by an amplification reaction using, as a core, a complex of the aforementioned analytical target and the aforementioned labeling substance used in detection binding to the aforementioned immobilizing reagent, so as to achieve high sensitivity. According to the present invention, a rapid and highly sensitive immunochromatography can be carried out.

Hereinafter, a sandwich method and a competitive method which are specific embodiments of the immunochromatography of the present invention, will be described.

In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled. The second antibody is immobilized on a suitable insoluble thin-membrane support (e.g. a nitrocellulose membrane, a glass fiber membrane, a nylon membrane, a cellulose membrane, etc.), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized second antibody, the analytical target (antigen) and the primary antibody, the labeled primary antibody that has not formed the aforementioned immune complex is removed. Subsequently, a metal ion and a reducing agent are supplied on a region of the insoluble thin-membrane support, on which the second antibody has been immobilized, so that a signal from the labeling substance of the labeled primary antibody that has formed the aforementioned immune complex may be amplified and detected. Otherwise, a metal ion and a reducing agent are added to the labeled primary antibody, and they are simultaneously added to the thin-membrane support, so that a signal from the labeling substance of the labeled primary antibody that has formed the aforementioned immune complex may be amplified, detected and measured.

In the competitive method, an analytical target can be analyzed by the following procedures, for example, but the procedures are not particularly limited thereto. The competitive method is known as a means for detecting a low molecular weight antigen which can not be assayed in the sandwich method. First, a primary antibody having specificity for an analytical target (an antigen) has previously been prepared. In addition, the primary antibody has previously been labeled with metal colloid or the like. An analytical target, or a compound which has a site which is similar with that of the analytical target and has a same epitope against the primary antibody as that of the analytical target, both of which can bind to the primary antibody, is immobilized on a suitable insoluble thin-membrane support (e.g. a nitrocellulose membrane, a glass fiber membrane, a nylon membrane, a cellulose membrane, etc.). It is then allowed to come into contact with a test sample (or an extract thereof) that is likely to contain the analytical target (the antigen). If the analytical target does not exist in the test sample, an antigen-antibody reaction occurs on the insoluble support between the labeled primary antibody, and the analytical target, or the compound which has a same epitope against the primary antibody as that of the analytical target, both of which can bind to the primary antibody. If the analytical target exists in the test sample, the analytical target (antigen) binds to the labeled primary antibody, and thus an antigen-antibody reaction on the insoluble support between the labeled primary antibody, and the analytical target, or the compound which has a same epitope against the primary antibody as that of the analytical target, both of which can bind to the primary antibody, is inhibited. Namely, binding by the antigen-antibody reaction does not occur.

After completion of the reaction of the immobilized substance which can bind to the primary antibody and the labeled primary antibody, the labeled primary antibody that has not formed the aforementioned immune complex is removed. Subsequently, a metal ion and a reducing agent are supplied to a region of the insoluble thin-membrane support, on which the substance which can bind to the primary antibody has been immobilized, for example, so that a signal from the labeling substance of the labeled primary antibody which formed immune complex may be amplified and detected. Otherwise, a metal ion and a reducing agent are added to the labeled primary antibody, and they are simultaneously added to the thin-membrane support, so that a signal from the labeling substance of the labeled secondary antibody that has formed the aforementioned immune complex may be amplified, detected and measured.

An amplification solution that can be used in the present invention is what is called a developing solution as described in publications common in the field of photographic chemistry (e.g. "*Kaitei Shashin kagaku no kiso, Ginen shashin hen* (Revised Basic Photographic Engineering, silver salt photography)," (the Society of Photographic Science and Technology of Japan, Colona Publishing Co., Ltd.); "*Shashin no kagaku* (Photographic Chemistry)," (Akira Sasaki, Shashin Kogyo Shuppan); "*Saishin Shoho Handbook* (Latest Formulation Handbook)," (Shinichi Kikuchi et al., Amiko Shuppan); etc.).

In the present invention, any type of amplification solution can be used, as long as it is what is called a physical developing solution, which comprises silver ions, and such silver ions in the solution act as a core of development and reduction is carried out using a metal colloid as a center.

The silver-containing compound used in the present invention may be an organic silver salt, an inorganic silver salt, or a silver complex.

The organic silver salt used in the present invention is an organic compound containing a reducible silver ion. Any one of an organic silver salt, an inorganic silver salt and a silver complex may be used as a compound containing a reducible silver ion in the present invention. For example, a silver nitrate, a silver acetate, a silver lactate, a silver butyrate, etc. have been known.

In addition, such a compound may be a silver salt or a coordination compound that forms a metallic silver relatively stable for light, when it is heated to 50° C. in the presence of a reducing agent.

The organic silver salt used in the present invention may be a compound selected from the silver salts of an azole compound and the silver salts of a mercapto compound. Such an azole compound is preferably a nitrogen-containing heterocyclic compound, and more preferably a triazole compound and a tetrazole compound. The mercapto compound is a compound having at least one mercapto group or thione group in the molecule thereof.

The silver salt of the nitrogen-containing heterocyclic compound of the present invention is preferably the silver salt of a compound having an imino group. Typical compounds include, but are not limited to, the silver salt of 1,2,4-triazole, the silver salt of benzotriazole or a derivative thereof (for example, a methylbenzotriazole silver salt and a 5-chlorobenzotriazole silver salt), a 1H-tetrazole compound such as phenylmercaptotetrazole described in U.S. Pat. No. 4,220,709, and imidazole or an imidazole derivative described in U.S. Pat. No. 4,260,677. Among these types of silver salts, a benzotriazole derivative silver salt or a mixture of two or more silver salts is particularly preferable.

The silver salt of the nitrogen-containing heterocyclic compound used in the present invention is most preferably the silver salt of a benzotriazole derivative.

The compound having a mercapto group or a thione group of the present invention is preferably a heterocyclic compound having 5 or 6 atoms. In this case, at least one atom in the ring is a nitrogen atom, and other atoms are carbon, oxygen, or sulfur atoms. Examples of such a heterocyclic compound include triazoles, oxazoles, thiazoles, thiazolines, imidazoles, diazoles, pyridines, and triazines. However, examples are not limited thereto.

Typical examples of the silver salt of the compound having a mercapto group or a thione group include, but are not limited to, the silver salt of 3-mercapto-4-phenyl-1,2,4-triazole, the silver salt of 2-mercapto-benzimidazole, the silver salt of 2-mercapto-5-aminothiazole, the silver salt of mercaptotriazine, the silver salt of 2-mercaptobenzoxazole, and the silver salt of compounds described in U.S. Pat. No. 4,123,274.

As such a compound having a mercapto group or a thione group of the present invention, a compound that does not contain a hetero ring may also be used. As such a mercapto or thione derivative that does not contain a hetero ring, an aliphatic or aromatic hydrocarbon compound having total 10 or more carbon atoms is preferable.

Among such mercapto or thione derivatives that do no contain a hetero ring, useful compounds include, but are not limited to, the silver salt of thioglycolic acid (for example, the silver salt of S-alkylthioglycolic acid having an alkyl group containing 12 to 22 carbon atoms) and the silver salt of dithiocarboxylic acid (for example, the silver salt of dithioacetic acid and the silver salt of thioamide).

An organic compound having the silver salt of carboxylic acid is also preferably used. It is straight-chain carboxylic acid, for example. Specifically, carboxylic acid containing 6 to 22 carbon atoms is preferably used. In addition, the silver salt of aromatic carboxylic acid is also preferable. Examples of such aromatic carboxylic acid and other carboxylic acids include, but are not limited to, substituted or unsubstituted silver benzoate (for example, silver 3,5-dihydroxybenzoate, silver o-methylbenzoate, silver m-methylbenzoate, silver p-methylbenzoate, silver 2,4-dichlorobenzoate, silver acetamide benzoate and silver p-phenylbenzoate), silver tannate, silver phthalate, silver terephthalate, silver salicylate, silver phenylacetate, and silver pyromellitate.

In the present invention, aliphatic acid silver containing a thioether group as described in U.S. Pat. No. 3,330,663 can also be preferably used. A soluble silver carboxylate having a hydrocarbon chain containing an ether bond or a thioether bond, or a soluble silver carboxylate having a sterically hindered substituent on an α-position (of the hydrocarbon group) or an ortho-position (of the aromatic group) can also be used. These silver carboxylates have an improved solubility in a coating solvent, which provides a coating material having little light scattering.

Such silver carboxylates are described in U.S. Pat. No. 5,491,059. All of the mixtures of the silver salts described therein can be used in the invention, as necessary.

The silver salt of sulfonate as described in U.S. Pat. No. 4,504,575 can also be used in the embodiment of the present invention.

Further, for example, the silver salt of acetylene described in U.S. Pat. No. 4,761,361 and No. 4,775,613 can also be used in the present invention. It can be provided as a core-shell type silver salt as described in U.S. Pat. No. 6,355,408. Such silver salt is composed of a core consisting of one or more silver salts and a shell consisting of one or more different silver salts.

In the present invention, another product useful as a non-photosensitive silver source is a silver dimer composite consisting of two different types of silver salts described in U.S. Pat. No. 6,472,131. Such a non-photosensitive silver dimer composite consists of two different types of silver salts. When the aforementioned two types of silver salts include a linear saturated hydrocarbon group as a silver ligand, a difference in the numbers of carbon atoms of the ligands is 6 or greater.

The organic silver salt is contained as silver generally in an amount of 0.001 to 0.2 mol/m$^2$, and preferably 0.01 to 0.05 mol/m$^2$, in terms of the silver amount.

The inorganic silver salt or the silver complex used in the present invention is a compound containing a reducible silver ion. Preferably, such an inorganic silver salt or a silver complex is an inorganic silver salt or a silver complex, which forms metallic silver relatively stable for light, when the salt or complex is heated to 50° C. or higher in the presence of a reducing agent.

Examples of the inorganic silver salt used in the present invention include: a silver halide (such as silver chloride, silver bromide, silver chlorobromide, silver iodide, silver chloroiodide, silver chloroiodobromide, and silver iodobromide); the silver salt of a silver thiosulfate (e.g. a sodium salt, a potassium salt, an ammonium salt, etc.); the silver salt of a silver thiocyanate (e.g. a sodium salt, a potassium salt, an ammonium salt, etc.); and the silver salt of a silver sulfite (e.g. a sodium salt, a potassium salt, an ammonium salt etc.).

The inorganic silver salt used in the present invention is preferably a silver halide or silver nitrate.

A method for forming the particles of the silver halide used in the invention is well known in the photographic industry. For example, methods described in Research Disclosure No. 17029, June 1978, and U.S. Pat. No. 3,700,458 may be used. Specifically, such a silver halide may be prepared by adding a silver-supplying compound (for example, a silver nitrate) and a halogen-supplying compound to a solution of a gelatin or other polymers.

The particle size of the silver halide is preferably very small in order to reduce examination noise. Specifically, the size is preferably 0.20 μm or less, more preferably 0.10 μm or less, and even more preferably in the range of nanoparticles. The term "particle size" is used herein to mean a diameter of a circular image having the same area as the projected area of the silver halide particle (the projected area of the main plane in the case of a tabular particle).

A silver thiosulfate, a silver thiocyanate, and a silver sulfite can also be prepared in the same manner as the formation of silver halide particles, by mixing a silver-supplying compound (such as a silver nitrate) with a thiosulfate (e.g. a sodium salt, a potassium salt, an ammonium salt, etc.), a thiocyanate (e.g. a sodium salt, a potassium salt, an ammonium salt, etc.), and a sulfite (e.g. a sodium salt, a potassium salt, an ammonium salt, etc.), respectively.

In general, if the concentration of silver ion in the amplification solution is too high, such silver ion is reduced in the amplification solution. In order to prevent such a phenomenon, a complexing agent may be used to cause the silver ion to form a complex. As such a complexing agent, amino acids such as glycine and histidine, heterocyclic bases, imidazole, benzimidazole, pyrazole, purine, pyridine, aminopyridine, nicotinamide, quinoline, and other similar aromatic heterocyclic compounds have been known. These compounds are described in E.P. Patent No. 0293947, for example. Further, as a complex salt-forming agent, thiosulfate, thiocyanate, and the like can also be used. Specific examples of the silver complex used in the present invention include a complex of a thiosulfate and a silver ion, a complex of a thiocyanate and a silver ion, a composite silver complex thereof, a complex of a sugar thione derivative and a silver ion, a complex of a cyclic imide compound (e.g. uracil, urazole, 5-methyluracil, barbituric acid, etc.) and a silver ion, and a complex of a 1,1-bissulfonylalkane and a silver ion. A preferred silver complex used in the invention is a complex of a cyclic imide compound (e.g. uracil, urazole, 5-methyluracil, barbituric acid, etc.) and a silver ion.

The silver complex used in the present invention may be prepared by a generally-known salt forming reaction. For example, the silver complex may be prepared by mixing in water or a water-miscible solvent a water-soluble silver supplier (such as a silver nitrate) with a ligand compound corresponding to the silver complex. The prepared silver complex can be used, after salts generated as by-products have been removed by a known desalting method such as dialysis or ultrafiltration.

The inorganic silver salt or the silver complex is contained as silver generally in an amount of 0.001 to 0.2 mol/m$^2$, and preferably 0.01 to 0.05 mol/m$^2$, in terms of the silver amount.

When an inorganic silver salt or a silver complex is used, a solvent for them is preferably used. The solvent used in the present invention is preferably a compound used as a ligand for forming a silver complex described in the above paragraphs for the "silver complex." Examples of such a compound used as a solvent in the present invention include a thiosulfate, a thiocyanate, a sugar thione derivative, a cyclic imide compound, and a 1,1-bissulfonylalkane. The solvent used in the present invention is more preferably a cyclic imide compound such as uracil, urazole, 5-methyluracil, or barbituric acid. The solvent used in the present invention is preferably used at a molar ratio of 0.1 to 10 moles with respect to silver ions.

As a reducing agent used for silver ion, either inorganic or organic materials capable of reducing silver(I) ion to silver, or the mixtures thereof, may be used.

As an inorganic reducing agent, reducible metal salts and reducible metal complex salts whose valence can be changed with metal ions such as $Fe^{2+}$, $V^{2+}$ or $Ti^{3+}$ have been known. These salts can be used in the present invention. When such an inorganic reducing agent is used, it is necessary to form a complex with the oxidized ion or reduce it, so as to remove or detoxify the oxidized ion. For example, in a system using $Fe^{+2}$ as a reducing agent, citric acid or EDTA is used to form a complex with $Fe^{3+}$ as an oxide, so as to detoxify it.

In the present system, such an inorganic reducing agent is preferably used. The metal salt of $Fe^{2+}$ is more preferable.

Developing agents used for wet-process silver halide photographic-sensitized materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), or other materials known to those skilled in the art (see, for example, U.S. Pat. No. 6,020,117 (Bauer et al.)) may be used in the present invention.

The term "ascorbic acid reducing agent" means a complex of ascorbic acid and a derivative thereof. Ascorbic acid reducing agents are described in many publications, as described below, including, for example, U.S. Pat. No. 5,236,816 (Purol et al.) and publications cited therein.

The reducing agent used in the present invention is preferably an ascorbic acid reducing agent. Useful ascorbic acid reducing agents include ascorbic acid, an analogue thereof, an isomer thereof, and a derivative thereof. Examples of such compounds include the following compounds. However, examples are not limited thereto.

Examples of such compounds include D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the art), and endiol-type ascorbic acid, enaminol-type ascorbic acid and thioenol-type ascorbic acid such as compounds described in U.S. Pat. No. 5,498,511, EP-A-0585,792, EP-A 0573700, EP-A 0588408, U.S. Pat. Nos. 5,089,819, 5,278,035, 5,384,232 and 5,376,510, JP 7-56286, U.S. Pat. No. 2,688,549, and Research Disclosure 37152 (March, 1995).

Among these compounds, D-, L-, and D,L-ascorbic acid (and an alkali metal salt thereof), and isoascorbic acid (and an alkali metal salt thereof) are preferable. Moreover, a sodium salt is a preferred salt thereof. If necessary, a mixture of these reducing agents may also be used.

A hindered phenol may be preferably used singly or in combination with one or more gradation-hardening reducing agents and/or contrast enhancers.

A hindered phenol is a compound having only one hydroxyl group on a benzene ring and also having at least one substituent at the ortho-position relative to the hydroxyl group. The hindered phenol reducing agent may have plural hydroxyl groups, as long as the hydroxyl groups are located on different benzene rings.

Examples of the hindered phenol reducing agent include binaphthols (that is, dihydroxybinaphthols), biphenols (that is, dihydroxybiphenols), bis(hydroxynaphthyl)methanes, bis(hydroxyphenyl)methanes (that is, bisphenols), hindered phenols, and hindered naphthols, each of which may be substituted.

Typical binaphthols include, but are not limited to, 1,1'-bi-2-naphthol, 1,1'-bi-4-methyl-2-naphthol, and compounds described in U.S. Pat. Nos. 3,094,417 and 5,262,295.

Typical biphenols include, but are not limited to, 2-(2-hydroxy-3-t-butyl-5-methylphenyl)-4-methyl-6-n-hexylphenol, 4,4'-dihydroxy-3,3,5,5-tetra-t-butylbiphenyl, 4,4'-dihydroxy-3,3',5,5'-tetramethylbiphenyl, and compounds described in U.S. Pat. No. 5,262,295.

Typical bis(hydroxynaphthyl)methanes include, but are not limited to, 4,4'-methylenebis(2-methyl-1-naphthol) and compounds described in U.S. Pat. No. 5,262,295.

Typical bis(hydroxyphenyl)methanes include, but are not limited to, bis(2-hydroxy-3-t-butyl-5-methylphenyl)methane (CAO-5), 1,1'-bis(2-hydroxy-3,5-dimethylphenyl)-3,5,5-trimethyl hexane (NONOX or PERMANAX WSO), 1,1'-bis(3,5-di-t-butyl-4-hydroxyphenyl)methane, 2,2'-bis(4-hydroxy-3-methylphenyl)propane, 4,4'-ethylidene-bis(2-t-butyl-6-methylphenol), 2,2'-isobutylidene-bis(4,6-dimethylphenol) (LOWINOX 221B46), 2,2'-bis(3,5-dimethyl-4-hydroxyphenyl)propane, and compounds described in U.S. Pat. No. 5,262,295.

Typical hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol, and 2-t-butyl-6-methylphenol.

Typical hindered naphthols include, but are not limited to, 1-naphthol, 4-methyl-1-naphthol, 4-methoxy-1-naphthol, 4-chloro-1-naphthol, 2-methyl-1-naphthol, and compounds described in U.S. Pat. No. 5,262,295.

Moreover, other compounds disclosed as reducing agents include amidoximes (for example, phenylamidoxime), 2-thienylamidoxime, p-phenoxyphenylamidoxime, a combination of an aliphatic carboxylic allyl hydrazide and ascorbic acid (for example, a combination of 2,2'-bis(hydroxymethyl)-propionyl-β-phenyl hydrazide and ascorbic acid), a combination of a polyhydroxybenzene and at least one of hydroxylamine, reductone and hydrazine (for example, a combination of hydroquinone and bis(ethoxyethyl)hydroxylamine), piperidi-4-methylphenylhydrazine, hydroxamic acids (for example, phenylhydroxamic acid, p-hydroxyphenylhydroxamic acid, and o-alaninehydroxamic acid), a combination of an azine and a sulfonamidophenol (for example, a combination of phenothiazine and 2,6-dichloro-4-benzenesulfonamidophenol), α-cyanophenylacetic acid derivatives (for example, ethyl-α-cyano-2-methylphenylacetic acid and ethyl-α-cyanophenylacetic acid), bis-o-naphthol (for example, 2,2'-dihydroxy-1-binaphthyl, 6,6'-dibromo-2,2'-dihydroxy-1,1'-binaphthyl, and bis(2-hydroxy-1-naphthyl) methane), a combination of bis-naphthol and a 1,3-dihydroxybenzene derivative (for example, 2,4-dihydroxybenzophenone and 2,4-dihydroxyacetophenone), 5-pyrazolones (for example, 3-methyl-1-phenyl-5-pyrazolone), reductones (for example, dimethylaminohexose reductone, anhydrodihydro-aminohexose reductone, and anhydrodihydro-piperidone-hexose reductone), indane-1,3- diones (for example, 2-phenylindane-1,3-dione), chromans (for example, 2,2-dimethyl-7-t-butyl-6-hydroxychroman), 1,4-dihydroxypyridines (for example, 2,6-dimethoxy-3,5-dicarbetoxy-1,4-dihydropyridine), ascorbic acid derivatives (1-ascorbic palmitate, ascorbic stearate), unsaturated aldehydes (ketones), and 3-pyrazolidones.

Examples of a reducing agent that can be used in the present invention include substituted hydrazines such as sulfonyl hydrazines described in U.S. Pat. No. 5,464,738. Other useful reducing agents are described, for example, in U.S. Pat. Nos. 3,074,809, 3,094,417, 3,080,254 and 3,887,417. Auxiliary reducing agents descried in U.S. Pat. No. 5,981,151 are also useful.

The reducing agent may be a combination of a hindered phenol reducing agent and a compound selected from various auxiliary reducing agents such as those mentioned below. In addition, a mixture of such a combined agent plus a contrast enhancer (that is, a mixture of the 3 components) is also useful. As such an auxiliary reducing agent, it is possible to use trityl hydrazide and formyl-phenyl hydrazide described in U.S. Pat. No. 5,496,695.

A contrast enhancer may be used in combination with the reducing agent. Useful contrast enhancers include, but are not limited to, hydroxylamines (including hydroxylamine and alkyl- and aryl-substituted derivatives thereof), alkanolamines and phthalic ammonium described in U.S. Pat. No. 5,545,505, hydroxamic acid compounds described in U.S. Pat. No. 5,545,507, N-acylhydrazine compounds described in U.S. Pat. No. 5,558,983, and hydrogen atom donor compounds described in U.S. Pat. No. 5,637,449.

Not all combinations of reducing agents and organic silver salts are equally effective. A preferred combination is a benzotriazole silver salt used as an organic silver salt, a substituted compound thereof or a mixture thereof, with an ascorbic acid reducing agent used as a reducing agent.

The reducing agent of the present invention may be contained in an amount of 1 mass % to 10 mass % (dry mass) based on the amount of silver in organic silver. When the reducing agent is added to a layer other than the layer containing the organic silver salt in a multilayer structure, the amount of the reducing agent is slightly higher, and it is desirably from approximately 2 mass % to approximately 15 mass %. An auxiliary reducing agent is contained in an amount of about 0.001 mass % to 1.5 mass % (dry weight).

Other auxiliary agents contained in the amplification solution may include a buffer, an antiseptic such as an antioxidant or an organic stabilizer, and a speed regulator. Examples of a buffer used herein include buffers comprising acetic acid, citric acid, sodium hydroxide, a salt thereof, or tris(hydroxymethyl)aminomethane, and other buffers used in ordinary chemical experiments. Using these buffers as appropriate, the pH of the amplification solution can be adjusted to the optimal pH.

The present invention will be more specifically described in the following examples. However, these examples are not intended to limit the scope of the present invention.

EXAMPLES

Comparative Example 1

Preparation and Evaluation of an Influenza Kit with Antibody Density of 0.004 µg/mm$^2$ and Gold Colloid Particle Diameter of 100 nm 1. Preparation of Anti-Influenza Antibody-Modified Gold Colloid (Particle Diameter: 100 nm)

1 mL of a 500 µg/mL anti-influenza type A virus antibody (Product No. 7307, Medix Biochemica) solution was added to a gold colloidal solution having pH adjusted by addition of 1 mL of a 20 mM Borax buffer (pH 9.0) to 9 mL of a 100 nm diameter gold colloidal solution (EM.GC100, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% NaN$_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified gold colloid (100 nm) solution was obtained.

2. Preparation of Gold Colloidal Antibody Holding Pad

Each antibody-modified gold colloid prepared in 1 was diluted into 5.6×10$^{10}$/mL with a coating solution for a gold colloid (20 mM Tris-Hcl buffer (pH 8.2), 0.05% PEG (Mw: 20000), and 5% sucrose) and water in such way that the ratio of (antibody-modified gold colloid):(coating solution for a gold colloid):(water) is 1:2:1. At this time, the OD at 520 nm is 7.0. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

3. Preparation of Antibody Immobilized Membrane (Antibody Density of 0.004 µg/mm$^2$)

An antibody-immobilized membrane was prepared in the following manner by immobilizing an antibody on a nitrocellulose membrane (HiFlow Plus HF120 with a plastic lining, Millipore) cut to the size of 25 mm×200 mm. The membrane, with one of its long sides facing downward, was coated with an anti-influenza type A virus antibody (for immobilization) (Product No. 7307, Medix Biochemica) solution prepared at a concentration of 0.5 mg/ml with the use of a coater of inkjet type ((BioDot Ltd.). Specifically, the membrane was coated so that a linear portion thereof 8 mm above the lower edge was coated to have a width of approximately 1 mm (the density of the antibody at the detection site was 0.004 µg/mm$^2$). In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 12 mm above the lower edge was coated (the density of the antibody at the control site was 0.04 µg/mm$^2$). The coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, 50 mM Tris-HCl, pH 7.5) in a similar vat and then allowed to stand therein for 30 minutes. The membrane was removed from the solution and then dried overnight at room temperature to prepare an antibody-immobilized membrane.

4. Construction of Kit

The antibody-immobilized membrane prepared in 3 above was adhered to a back pressure-sensitive adhesive sheet (AR-care9020, NIPPN TechnoCluster, Inc.). At this time, the membrane was used with the anti-influenza antibody line side (one of the long sides of the membrane) facing downward. The gold colloidal antibody holding pad prepared in 2 above was adhered onto the antibody-immobilized membrane such that the pad overlapped the lower portion of the antibody-immobilized membrane by approximately 2 mm. The sample addition pad (glass fiber pad (Glass Fiber Conjugate Pad, Millipore) cut to the size of 18 mm×150 mM was adhered to the gold colloidal antibody holding pad such that the sample addition pad overlapped the lower portion of the gold colloidal antibody holding pad by approximately 4 mm. Absorbent pads (cellulose membrane cut to the size of 5 mm×100 mm (Cellulose Fiber Sample Pad, Millipore)) were adhered onto the antibody-immobilized membrane such that the absorbent pads overlapped the upper portion of the antibody-immobilized membrane by approximately 5 mm. With the use of a guillotine cutter (CM4000, NIPPN 1. TechnoCluster, Inc.), the thus overlapped and adhered members of the long sides were cut in parallel to the short sides of the overlapped members at 5-mm intervals, whereby immunochromatographic strips were prepared. These strips were placed in a plastic case (NIPPN TechnoCluster, Inc.), so as to prepare an immunochromatography kit for testing.

5. Method for Measurement of Nonspecific Adsorption Level

PBS buffer containing 1% BSA was prepared, and 100 μL of the PBS buffer was added to the test immunochromatography kit prepared by the above methods 1 to 4. 15 minutes later, strips were removed from the plastic case, and a water absorption pad was removed. Then, a new water absorption pad (cellulose membrane cut to the size of 5 mm×100 mm) was adhered by twisting it with Sellotape. This strip was then placed in a microtube containing 700 μL of PBS buffer containing 1% BSA in such a way that a sample addition site is immersed in a solution, and was allowed to stand for 1 hour, so as to wash the membrane. Subsequently, the strip was removed from the tube, and pads were removed. Then, a portion containing "detection site (line portion) of 2.0 mm width (line portion is 1 mm width, and the upstream (0.5 mm) and the downstream (0.5 mm) are contained), and "non-detection site on porous carrier (non-line portion)" (intermediate site between "line portion" and control site) of 2.0 mm width, were cut out. The amount of gold at each site was quantified by HR-ICP-MS (Model No. Element XR, Thermo Fisher Scientific Co.). Further, the length of side of each site which was cut out was measured by caliper square, and the amount of non-specifically adsorbed gold at only "line portion" was calculated from the density of non-specifically adsorbed gold at "non-line portion".

6. Method for Measurement of the Detection Sensitivity (6-1) Preparation of a Silver Amplification Solution (i) Preparation of Amplification Solution-1

40 mL of an aqueous solution of 1 mol/L iron nitrate prepared by dissolving iron nitrate (III) nonahydrate (manufactured by Wako Pure Chemical Industries, Ltd.; 095-00995) in water, 10.5 g of citric acid (manufactured by Wako Pure Chemical Industries, Ltd.; 038-06925), 0.1 g of dodecylamine (manufactured by Wako Pure Chemical Industries, Ltd.; 123-00246), and 0.1 g of $C_9H_{19}$—$C_6H_4$—O—$(CH_2CH_2O)_{50}$H were dissolved in 325 g of water. After all the compounds had been fully dissolved in the water, 40 mL of nitric acid (10%) was added to the mixed solution, while it was stirred with a stirrer 80 mL of this solution was weighed, and 11.76 g of iron (II) ammonium sulfate hexahydrate (manufactured by Wako Pure Chemical Industries, Ltd.; 091-00855) was then added to the solution, thereby obtaining Amplification solution-1.

(ii) Preparation of Amplification Solution-2

Water was added to 10 mL of a silver nitrate solution (containing 10 g of silver nitrate) to a total amount of 100 g, thereby preparing Amplification solution-2 (a 10%-by-weight silver nitrate aqueous solution).

(iii) Preparation of Amplification Solution 40 mL of Amplification solution-1 was weighted, and 4.25 mL of Amplification solution-2 was added thereto, and a mixture was stirred to obtain Amplification solution.

(6-2) Method for Evaluation of the Detection Sensitivity (i) Setting of Amplification Time 100 μl of PBS buffer containing 1% BSA was added dropwise to the prepared immunochromatography kit, and the kit was left stand for 15 minutes. Then, the strips were removed from the plastic case, and a water absorption pad was removed. Then, a new water absorption pad (cellulose membrane cut to the size of 5 mm×100 mm) was adhered by twisting it with Sellotape. This strip was then placed in a microtube containing 700 μL of washing buffer (PBS buffer containing 1% BSA), and was allowed to stand for 1 hour, so as to wash the membrane. Subsequently, the water absorption pad which was previously fixed to the strip was removed. 40 ml of the amplification solution was added to a balance dish (150 mm×105 mm×15 mm), and the immunochromatography strip was immersed therein and stirred to perform amplification. The time when the strip was added to the amplification solution was defined as 0 minute, and amplification was performed until the line of detection site can be detected visually, and the time until it was measured. Immediately after amplification, the strip was washed with water. The line which was detected at this time is due to the non-specifically adsorbed gold. Therefore, as the time where the line cannot be detected due to the non-specifically adsorbed gold, "(the time where the line was detected without an antigen)-30 seconds" was defined as the amplification time. When "the time where the line was detected without an antigen" is less than 30 seconds, it was regarded as a false positive, and the detection sensitivity was not measured.

(ii) Measurement of Detection Sensitivity

BD Flu Egzaman control A+B− (Becton, Dickinson and Company) was dissolved in PBS buffer containing 1% BSA to prepare an antigen diluted solution. This antigen diluted solution was dotted onto the immunochromatography kit in the same way as in (6-2) (i), and washing was carried out. An amplification was carried out for the time which was set in (6-2) (i), and the antigen concentration limit at which a line at the detection portion could be observed visually was defined as the detection sensitivity for the kit.

Comparative Example 2

Preparation and Evaluation of an Influenza Kit with Antibody Density of 1.4 μg/mm$^2$ and Gold Colloid Particle Diameter of 10 nm An immunochromatography kit was prepared in the same way as in 1 to 4 of Comparative example 1, provides that the concentration of antibody which is coated on the membrane was set to be 20 mg/mL to prepare an antibody-immobilized membrane (line width of 1 mm, and the antibody density of 1.4 µg/mm²). This immunochromatography kit was evaluated in the same way as in 5 and 6 of Comparative example 1.

Example 1

Preparation and Evaluation of an Influenza Kit with Antibody Density of 0.11 µg/mm², Gold Colloid Particle Diameter of 50 nm, and F(ab')2 Fragment as an Antibody for Gold Colloid 1. Preparation of $F(ab')_2$ Fragment Anti-Influenza Type A Virus Antibody An $F(ab')_2$ fragment anti-influenza type A virus antibody was prepared using an anti-influenza type A virus antibody (Product No. 7307, Medix Biochemica) and an ImmunoPure® IgG1 Fab and $F(ab')_2$ Preparation Kit (Product No. 44880, Pierce).

2. Preparation of Kit Using $F(ab')_2$ Fragment Anti-Influenza Virus Antibody-Modified Gold Colloid An antibody-modified gold colloidal (50 nm) solution was similarly prepared using type A antibody prepared in 1, as follows.

1 mL of a 170 µg/mL $F(ab')_2$ fragment antibody solution was added to a gold colloidal solution having pH adjusted by addition of 1 mL of a 20 mM Borax buffer (pH 8.5) to 9 mL of a 50-nm diameter gold colloidal solution (EMGC50, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. Subsequently, 1.1 mL of a 10% bovine serum albumin (BSA FractionV, Product No. A-7906, SIGMA) aqueous solution was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified gold colloidal (50 nm) solution was obtained.

3. Preparation of Gold Colloidal Antibody Holding Pad

Each antibody-modified gold colloid prepared in 2 was diluted into $5.6×10^{10}$/mL with a coating solution for a gold colloid (20 mM Tris-Hcl buffer (pH 8.2), 0.05% PEG (Mw: 20000), and 5% sucrose) and water in such way that the ratio of (antibody-modified gold colloid):(coating solution for a gold colloid):(water) is 1:2:1. At this time, the OD at 520 nm is 1.5. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

4. Preparation and Evaluation of a Kit with Anti-Influenza Virus Antibody-Modified Gold Colloid An immunochromatography kit was prepared in the same way as in 4 of Comparative example 1, provides that the concentration of antibody which is coated on the membrane was set to be 1.5 mg/mL to prepare an antibody-immobilized membrane (line width of 1 mm, and the antibody density of 0.11 µg/mm²) in the same way as in 3 of Comparative example 1 and $F(ab')_2$ fragment anti-influenza virus antibody-modified gold colloid (particle diameter of 50 nm) prepared in 1 and 2 of Example 1 was used. This immunochromatography kit was evaluated in the same way as in 5 and 6 of Comparative example 1.

Example 2

Preparation and Evaluation of an Influenza Kit with Antibody Density of 0.005 µg/mm², Gold Colloid Particle Diameter of 100 nm, and $F(ab')_2$ Fragment as an Antibody for Antibody Immobilized Membrane 1. Preparation of F(ab')2 Fragment Antibody Immobilized Membrane (Antibody Density of 0.005 µg/mm²)

F(ab')2 fragment anti-influenza type A antibody was prepared in the same way as in Example 1, and the concentration was adjusted to 0.7 mg/mL. Using it, an antibody immobilized membrane was prepared as in Comparative example 1 (line width of 1 mm, and antibody density of 0.005 µg/mm²).

2. Preparation and Evaluation of a Kit with F(ab')2 Fragment Anti-Influenza Virus Antibody-Modified Gold Colloid An immunochromatography kit was prepared in the same way as in 1, 2 and 4 of Comparative example 1, provides that $F(ab')_2$ fragment antibody immobilized membrane prepared in 1 of Example 2 was used. This immunochromatography kit was evaluated in the same way as in 5 and 6 of Comparative example 1.

Example 3

Preparation and Evaluation of an Influenza Kit with Antibody Density of 1.4 µg/mm², Gold Colloid Particle Diameter of 15 nm, and F(ab')2 Fragment as an Antibody for Gold Colloid 1. Preparation of Kit Using $F(ab')_2$ Fragment Anti-Influenza Virus Antibody-Modified Gold Colloid $F(ab')_2$ fragment anti-influenza virus type A antibody was prepared in the same way as in 1 of Example 1, and an antibody-modified gold colloid was prepared as follows.

1 mL of a 500 µg/mL $F(ab')_2$ fragment antibody solution was added to a gold colloidal solution having pH adjusted by addition of 1 mL of a 50 mM $KH_2PO_4$ buffer (pH 8.0) to 9 mL of a 15-nm diameter gold colloidal solution (EMGC15, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. Subsequently, 1.1 mL of a 10% bovine serum albumin (BSA FractionV, Product No. A-7906, SIGMA) aqueous solution was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% $NaN_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified gold colloidal (15 nm) solution was obtained.

2. Preparation of Gold Colloidal Antibody Holding Pad

Each antibody-modified gold colloid prepared in 1 was diluted into $5.6×10^{10}$/mL with a coating solution for a gold colloid (20 mM Tris-Hcl buffer (pH 8.2), 0.05% PEG (Mw: 20000), and 5% sucrose) and water in such way that the ratio of (antibody-modified gold colloid):(coating solution for a gold colloid):(water) is 1:2:1. At this time, the OD at 520 nm is 0.032. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

3. Preparation and Evaluation of a Kit with Anti-Influenza Virus Antibody-Modified Gold Colloid An immunochromatography kit was prepared in the same way as in 4 of Comparative example 1, provides that the concentration of antibody which is coated on the membrane was set to be 20 mg/mL to prepare an antibody-immobilized membrane (line width of 1 mm, and the antibody density of 1.4 µg/mm$^2$) in the same way as in 3 of Comparative example 1 and F(ab')$_2$ fragment anti-influenza virus antibody-modified gold colloid (particle diameter of 15 nm) prepared in 2 of Example 3 was used. This immunochromatography kit was evaluated in the same way as in 5 and 6 of Comparative example 1.

Comparative Example 3

Preparation and Evaluation of an Influenza Kit with Antibody Density of 1.4 µg/mm$^2$ and Gold Colloid Particle Diameter of 15 nm An immunochromatography kit was prepared in the same way as in 3 of Example 3, provides that the concentration of antibody which is coated on the membrane was set to be 20 mg/mL to prepare an antibody-immobilized membrane (line width of 1 mm, and the antibody density of 1.4 µg/mm$^2$). This immunochromatography kit was evaluated in the same way as in 5 and 6 of Comparative example 1.

From the results of Examples 1 to 3 and Comparative examples 1 to 3, it was shown that if "amount of non-specific adsorption of line portion (L)/amount of non-specifically adsorbed gold of non-line portion (BG)" is less than 0.4, the detection sensitivity is low; if "L/BG" is more than 2.5, false positive signal may occur and the detection sensitivity is too low even without false positive signal. Therefore, it is preferred that "L/BG" is 0.4 to 2.5 (Table 1). Further, if the nonspecifically adsorbed density is more than 10$^6$/mm$^2$, the detection sensitivity is too low. If the nonspecifically adsorbed density is more than 10$^5$/mm$^2$, the detection sensitivity is low slightly (Table 1). Therefore, in the present invention, the nonspecifically adsorbed density is 10$^6$/mm$^2$ or less, and preferably the nonspecifically adsorbed density is 10$^5$/mm$^2$ or less. In order to satisfy such requirement, it is necessary that either of an antibody for gold colloid and an antibody for membrane is F(ab')2 (Table 1).

Example 4

Preparation and Evaluation of an Influenza Kit with Antibody Density of 0.02 µg/mm$^2$, Gold Colloid Particle Diameter of 50 nm and F(ab')2 Fragment as an Antibody for Gold Colloid An immunochromatography kit was prepared and evaluated in the same way as in Example 1, provides that the concentration of antibody which is coated on the membrane was set to be 0.3 mg/mL to prepare an antibody-immobilized membrane (line width of 1 mm, and the antibody density of 0.02 µg/mm$^2$).

Example 5

Preparation and Evaluation of an Influenza Kit with Antibody Density of 0.02 µg/mm$^2$, Gold Colloid Particle Diameter of 50 nm and F(ab')2 Fragment as an Antibody for Gold Colloid and an Antibody for Antibody-Immobilized Membrane An immunochromatography kit was prepared and evaluated in the same way as in Example 1, provides that an antibody-immobilized membrane (line width of 1 mm, and the antibody density of 0.02 µg/mm$^2$) was prepared in the same way as in Example 2 using F(ab')2 fragment antibody, the concentration of whish was adjusted to be 0.3 mg/mL.

Example 6

Preparation and Evaluation of an Influenza Kit with Antibody Density of 0.02 µg/mm$^2$, Gold Colloid Particle Diameter of 50 nm, and F(ab')2 Fragment as an Antibody for Antibody-Immobilized Membrane 1. Preparation of Anti-Influenza Virus Antibody-Modified Gold Colloid 1 mL of a 90 µg/mL anti-influenza type A virus antibody (Product No. 7307, Medix Biochemica) solution was added to a gold colloidal solution having pH adjusted by addition of 1 mL of a 50 mM KH$_2$PO$_4$ buffer (pH 7.5) to 9 mL of a 50 nm diameter gold colloidal solution (EM.GC50, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA FractionV, Product No. A-7906, SIGMA) aqueous solution (1.1 mL) was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% NaN$_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified gold colloid (100 nm) solution was obtained.

2. Preparation and Evaluation of a Kit with Anti-Influenza Virus Antibody-Modified Gold Colloid An immunochromatography kit was prepared and was evaluated in the same way as in Comparative example 1, provides that an antibody-immobilized membrane (line width of 1 mm, and the antibody density of 0.02 µg/mm$^2$) was prepared in the same way as in Example 2 using F(ab')2 fragment antibody, the concentration of whish was adjusted to be 0.3 mg/mL, and anti-influenza virus antibody-modified gold colloid (particle diameter of 50 nm) prepared in 1 of Example 6 was used.

From the results of Examples 4 to 6, it was found that the detection sensitivity is higher in the case where F(ab')2 fragment antibody was used as an antibody for gold colloid (Table 2).

Example 7

Preparation and Evaluation of an Influenza Kit with Antibody Density of 0.007 µg/mm$^2$, Gold Colloid Particle Diameter of 20 nm, and F(ab')2 Fragment as an Antibody for Gold Colloid and an Antibody for Antibody-Immobilized Membrane 1. Preparation of F(ab')2 Fragment Anti-Influenza Virus Antibody-Modified Gold Colloid F(ab')$_2$ fragment anti-influenza virus type A antibody was prepared in the same way as in 1 of Example 1, and an antibody-modified gold colloid was prepared as follows.

1 mL of a 300 µg/mL F(ab')$_2$ fragment antibody solution was added to a gold colloidal solution having pH adjusted by addition of 1 mL of a 50 mM KH$_2$PO$_4$ buffer (pH 8.0) to 9 mL of a 20-nm diameter gold colloidal solution (EMGC20, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. Subsequently, 1.1 mL of a 10% bovine serum albumin (BSA FractionV, Product No. A-7906, SIGMA) aqueous solution was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% NaN$_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified gold colloidal (20 nm) solution was obtained.

2. Preparation of Gold Colloidal Antibody Holding Pad

Each antibody-modified gold colloid prepared in 1 was diluted into 5.6×10$^{10}$/mL with a coating solution for a gold colloid (20 mM Tris-Hcl buffer (pH 8.2), 0.05% PEG (Mw: 20000), and 5% sucrose) and water in such way that the ratio of (antibody-modified gold colloid):(coating solution for a gold colloid):(water) is 1:2:1. At this time, the OD at 520 nm is 0.080. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

3. Preparation and Evaluation of a Kit with Anti-Influenza Virus Antibody-Modified Gold Colloid An immunochromatography kit was prepared in the same way as in 4 of Comparative example 1, provides that an antibody-immobilized membrane (line width of 1 mm, and the antibody density of 0.007 µg/mm$^2$) was prepared in the same way as in Example 2 using F(ab')2 fragment antibody, the concentration of whish was adjusted to be 0.1 mg/mL, and F(ab')2 fragment anti-influenza virus antibody-modified gold colloid (particle diameter of 20 nm) prepared in 2 of Example 7 was used. This immunochromatography kit was evaluated in the same way as in 5 and 6 of Comparative example 1.

Example 8

Preparation and Evaluation of an Influenza Kit with Antibody Density of 0.007 µg/mm$^2$, Gold Colloid Particle Diameter of 80 nm, and F(ab')2 Fragment as an Antibody for Gold Colloid and an Antibody for Antibody-Immobilized Membrane 1. Preparation of F(ab')$_2$ Fragment Anti-Influenza Virus Antibody-Modified Gold Colloid F(ab')$_2$ fragment anti-influenza virus type A antibody was prepared in the same way as in 1 of Example 1, and an antibody-modified gold colloid was prepared as follows.

1 mL of a 500 µg/mL F(ab')$_2$ fragment antibody solution was added to a gold colloidal solution having pH adjusted by addition of 1 mL of a 50 mM KH$_2$PO$_4$ buffer (pH 7.0) to 9 mL of a 80-nm diameter gold colloidal solution (EMGC80, BBI), followed by agitation. The mixture was allowed to stand for 10 minutes and then 550 µL of 1% polyethylene glycol (PEG Mw. 20000, Product No. 168-11285, Wako Pure Chemical Industries, Ltd.) aqueous solution was added to the mixture, followed by agitation. Subsequently, 1.1 mL of a 10% bovine serum albumin (BSA FractionV, Product No. A-7906, SIGMA) aqueous solution was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% NaN$_3$) and then centrifuged again at 8000×g and 4° C. for 30 minutes. The supernatant was removed so that approximately 1 mL of the solution remained. The gold colloids were dispersed again using an ultrasonic washing machine, so that an antibody-modified gold colloidal (80 nm) solution was obtained.

2. Preparation of Gold Colloidal Antibody Holding Pad

Each antibody-modified gold colloid prepared in 1 was diluted into 5.6×10$^{10}$/mL with a coating solution for a gold colloid (20 mM Tris-Hcl buffer (pH 8.2), 0.05% PEG (Mw: 20000), and 5% sucrose) and water in such way that the ratio of (antibody-modified gold colloid):(coating solution for a gold colloid):(water) is 1:2:1. At this time, the OD at 520 nm is 4.6. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

3. Preparation and Evaluation of a Kit with Anti-Influenza Virus Antibody-Modified Gold Colloid An immunochromatography kit was prepared and evaluated in the same way as in Example 7, provides that an antibody-immobilized membrane (line width of 1 mm, and the antibody density of 0.007 µg/mm$^2$) was prepared in the same way as in Example 7 using F(ab')2 fragment antibody, the concentration of whish was adjusted to be 0.1 mg/mL, and F(ab')2 fragment anti-influenza virus antibody-modified gold colloid (particle diameter of 80 nm) prepared in 2 of Example 8 was used.

Example 9

Preparation and Evaluation of an Influenza Kit with Antibody Density of 0.007 µg/mm$^2$, Gold Colloid Particle Diameter of 15 nm, and F(ab')2 Fragment as an Antibody for Gold Colloid and an Antibody for Antibody-Immobilized Membrane An immunochromatography kit was prepared and evaluated in the same way as in Example 3, provides that an antibody-immobilized membrane (line width of 1 mm, and the antibody density of 0.007 μg/mm²) was prepared in the same way as in Example 7 using F(ab')2 fragment antibody, the concentration of whish was adjusted to be 0.1 mg/mL.

Example 10

Preparation and Evaluation of an Influenza Kit with Antibody Density of 0.007 μg/mm², Gold Colloid Particle Diameter of 100 nm, and F(ab')2 Fragment as an Antibody for Gold Colloid and an Antibody for Antibody-Immobilized Membrane 1. Preparation of F(ab')$_2$ Fragment Anti-Influenza Virus Antibody-Modified Gold Colloid F(ab')$_2$ fragment anti-influenza virus type A antibody was prepared in the same way as in 1 of Example 1, and an antibody-modified gold colloid was prepared as follows.

1 mL of a 1000 μg/mL F(ab')$_2$ fragment antibody solution was added to a gold colloidal solution having pH adjusted by addition of 1 mL of a 20 mM Borax buffer (pH 8.5) to 9 mL of a 100-nm diameter gold colloidal solution (EMGC100, BBI), followed by agitation. The mixture was allowed to stand for 10 minutes and then 550 μL of 1% polyethylene glycol (PEG Mw. 20000, Product No. 168-11285, Wako Pure Chemical Industries, Ltd.) aqueous solution was added to the mixture, followed by agitation. Subsequently, 1.1 mL of a 10% bovine serum albumin (BSA FractionV, Product No. A-7906, SIGMA) aqueous solution was added to the resultant, followed by agitation. The solution was centrifuged at 8000×g and 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw. 20000), 150 mM NaCl, 1% BSA, and 0.1% NaN$_3$) and then centrifuged again at 5000×g and 4° C. for 30 minutes. The supernatant was removed so that approximately 1 mL of the solution remained. The gold colloids were dispersed again using an ultrasonic washing machine, so that an antibody-modified gold colloidal (100 nm) solution was obtained.

2. Preparation of Gold Colloidal Antibody Holding Pad

Each antibody-modified gold colloid prepared in 1 was diluted into 5.6×10$^{10}$/mL with a coating solution for a gold colloid (20 mM Tris-Hcl buffer (pH 8.2), 0.05% PEG (Mw: 20000), and 5% sucrose) and water in such way that the ratio of (antibody-modified gold colloid):(coating solution for a gold colloid):(water) is 1:2:1. At this time, the OD at 520 nm is 7.0. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

3. Preparation and Evaluation of a Kit with Anti-Influenza Virus Antibody-Modified Gold Colloid An immunochromatography kit was prepared and evaluated in the same way as in Example 7, provides that an antibody-immobilized membrane (line width of 1 mm, and the antibody density of 0.007 μg/mm²) was prepared in the same way as in Example 7 using F(ab')2 fragment antibody, the concentration of whish was adjusted to be 0.1 mg/mL, and F(ab')2 fragment anti-influenza virus antibody-modified gold colloid holding pad (particle diameter of 100 nm) prepared in 2 of Example 10 was used.

From the results of Examples 7 to 10, it was found that the detection sensitivity is higher in the case where the particle diameter of gold colloid is 20 nm to 80 nm. If the particle diameter of gold colloid is less than 20 nm or more than 80 nm, the detection sensitivity decreases slightly (Table 3).

Example 11

Preparation and Evaluation of an Influenza Kit with Antibody Density of 0.006 μg/mm², Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 0.09 mg/ml and an antibody-immobilized membrane (line width of 1 mm, and the antibody density of 0.006 μg/mm²) was prepared

Example 12

Preparation and Evaluation of an Influenza Kit with Antibody Density of 0.007 μg/mm², Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 0.1 mg/ml and an antibody-immobilized membrane (line width of 1 mm, and the antibody density of 0.007 μg/mm²) was prepared

Example 13

Preparation and Evaluation of an Influenza Kit with Antibody Density of 0.014 g/mm², Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 0.2 mg/ml and an antibody-immobilized membrane (line width of 1 mm, and the antibody density of 0.014 μg/mm²) was prepared

Example 14

Preparation and Evaluation of an Influenza Kit with Antibody Density of 0.021 μg/mm², Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 0.3 mg/ml and an antibody-immobilized membrane (line width of 1 mm, and the antibody density of 0.021 μg/mm²) was prepared

Example 15

Preparation and Evaluation of an Influenza Kit with Antibody Density of 0.63 μg/mm², Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 9.0 mg/ml and an antibody-immobilized membrane (line width of 1 mm, and the antibody density of 0.63 µg/mm$^2$) was prepared

Example 16

Preparation and Evaluation of an Influenza Kit with Antibody Density of 0.84 µg/mm$^2$, Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 12.0 mg/ml and an antibody-immobilized membrane (line width of 1 mm, and the antibody density of 0.84 µg/mm$^2$) was prepared

Example 17

Preparation and Evaluation of an Influenza Kit with Antibody Density of 1.1 µg/mm$^2$, Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 16.0 mg/ml and an antibody-immobilized membrane (line width of 1 mm, and the antibody density of 1.1 µg/mm$^2$) was prepared

Example 18

Preparation and Evaluation of an Influenza Kit with Antibody Density of 1.2 µg/mm$^2$, Gold Colloid Particle Diameter of 50 nm, and F(ab')2 Fragment as an Antibody for Gold Colloid An immunochromatography kit was prepared and evaluated in the same way as in Example 1, provides that the concentration of the antibody for coating on the membrane was set to be 17.0 mg/ml and an antibody-immobilized membrane (line width of 1 mm, and the antibody density of 1.2 µg/mm$^2$) was prepared From the results of Examples 11 to 18, it was found that the detection sensitivity is high in the antibody density of 0.007 µg/mm$^2$ to 1.1 µg/mm$^2$, and the detection sensitivity is higher in the antibody density of 0.014 µg/mm$^2$ to 0.84 µg/mm$^2$, and the detection sensitivity is still higher in the antibody density of 0.021 µg/mm$^2$ to 0.63 µg/mm$^2$ (Table 4).

Example 19

Preparation and Evaluation of an Influenza Kit with Antibody Density of 0.11 µg/mm$^2$, Gold Colloid Particle Diameter of 50 nm, F(ab')2 Fragment as an Antibody for Gold Colloid, and Polyethylene Membrane 1. Preparation of an Antibody Immobilized Polyethylene Piece (Antibody Density of 0.11 µg/mm$^2$)

Anti-influenza type A virus antibody (Product No. 7307, Medix Biochemica)) was immobilized on latex microsphere (Bangs Laboratories Inc.) having a particle size of 0.3 µm by the method described in Adsorption to Microspheres (Technote 204, Bangs Laboratories Inc.) to prepare an antibody immobilized latex microsphere (47.6 µg of antibody was immobilized per 1 mg of particle). This antibody immobilized latex micro sphere was adjusted to 1.5% (=0.015 mg/µl). 3 µl of it was spotted at the center of polyethylene piece (AQ800, 0.5 cm×2.5 cm×0.1 cm; ASAHI KASEI CHEMICAL), and was dried at 37° C. for 30 minutes to prepare an antibody immobilized polyethylene piece. The detection site is a circle having a diameter of 5 mm, and the antibody density is 0.11 µg/mm$^2$.

2. Preparation of F(ab')2 Fragment Anti-Influenza Virus Antibody Modified Gold Colloid and Gold Colloid Antibody Holding Pad, and Construction and Evaluation of Kit F(ab')2 fragment anti-influenza virus antibody modified gold colloid holding pad was prepared in the same way as in Example 1.

For construction of a kit, the antibody-immobilized membrane prepared in 1 above was adhered to a back pressure-sensitive adhesive sheet (ARcare9020, NIPPN TechnoCluster, Inc.) cut into 5 mm width. The gold colloidal antibody holding pad was adhered onto one side of the antibody-immobilized polyethylene piece such that the pad overlapped the piece by approximately 2 mm. The sample addition pad (glass fiber pad (Glass Fiber Conjugate Pad, Millipore) cut to the size of 18 mm×150 mm was adhered to the gold colloidal antibody holding pad such that the sample addition pad overlapped the lower portion of the gold colloidal antibody holding pad by approximately 4 mm. Absorbent pads (cellulose membrane cut to the size of 5 mm×20 mm (Cellulose Fiber Sample Pad, Millipore)) were adhered onto the other side of the antibody-immobilized polyethylene piece such that the absorbent pads overlapped the piece by approximately 5 mm, whereby immunochromatographic strips were prepared. These strips were placed in a plastic case (NIPPN Techno-Cluster, Inc.), so as to prepare an immunochromatography kit for testing.

Evaluation was carried out in the same way as in Example 1.

Example 20

Preparation and Evaluation of an Influenza Kit with Antibody Density of 0.11 µg/mm$^2$, Gold Colloid Particle Diameter of 50 nm, F(ab')2 Fragment as an Antibody for Gold Colloid, and Nylon 66 Membrane 1. Preparation of Antibody Immobilized Nylon Membrane (Antibody Density of 0.11 µg/mm$^2$)

An antibody-immobilized membrane was prepared in the following manner by immobilizing an antibody on a nylon membrane (Immunodye ABC, pore size: 3.0 µm, Nihon Pall Ltd) cut to the size of 25 mm×200 mm. The membrane, with one of its long sides facing downward, was coated with an anti-influenza type A virus antibody (for immobilization) (Product No. 7307, Medix Biochemica) solution prepared at a concentration of 1.5 mg/ml with the use of a coater of inkjet type (BioDot Ltd.) in 0.7 µl/cm. Specifically, the membrane was coated so that a linear portion thereof 8 mm above the lower edge was coated to have a width of approximately 1 mm. In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 14 mm above the lower edge was coated (the density of the antibody at the control site was 0.035 µg/mm$^2$). The coated membrane was dried at 50° C. for 30 minutes with a hot-air dryer. The membrane was immersed in 500 ml of a blocking solution (50 mM borate buffer (pH 8.5) containing 0.5 w % cascin (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, 50 mM Tris-HCl, pH 7.5) in a similar vat and then allowed to stand therein for 30 minutes. The membrane was removed from the solution and then dried overnight at room temperature to prepare an antibody-immobilized membrane.

An immunochromatography kit was prepared and evaluated in the same way as in Example 1, including preparation of F(ab')2 fragment anti-influenza virus antibody modified gold colloid.

From the results of Examples 1, 19 and 20, the detection sensitivity is higher in the case where nitrocellulose or polyethylene was used as a material of an antibody immobilized membrane (Table 5).

Figure 3:
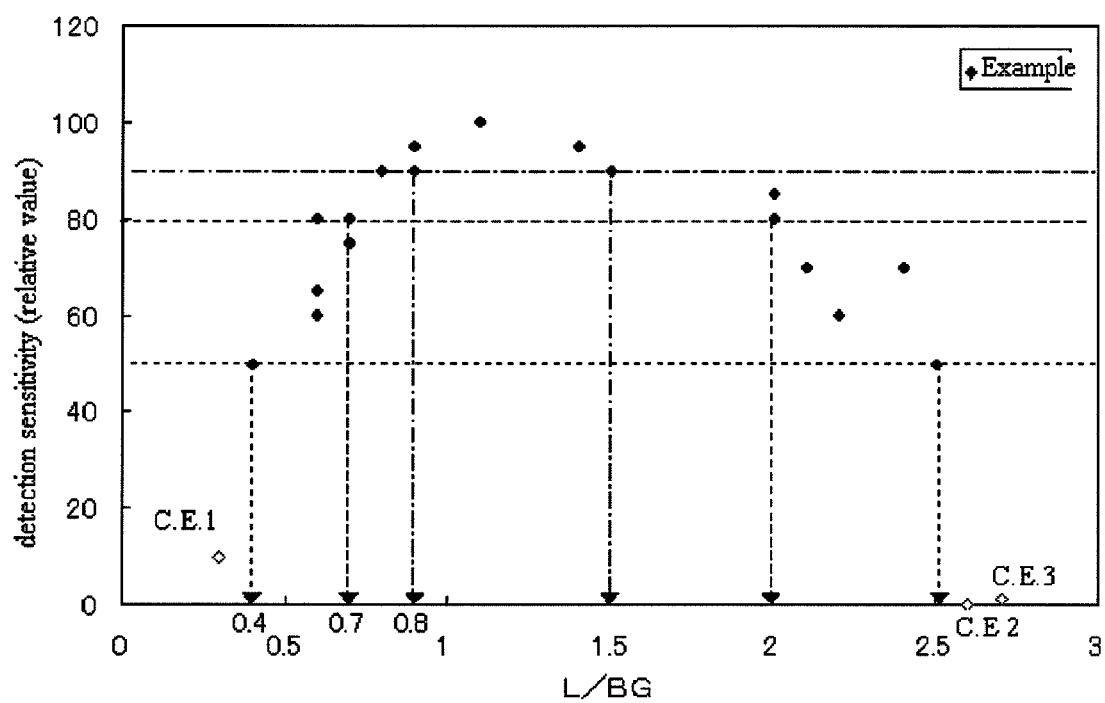
FIG. 3 is the relationship between the detection sensitivity and L/BG in Examples 1 to 21 and Comparative Examples 1 to 3
1: Back pressure-sensitive adhesive sheet
2: Gold colloidal antibody holding pad
3: Antibody-immobilized membrane
3a: Capture site
31: Detection part
32: Control part
4: Absorbent pad
5: Sample addition pad
10: Immunochromatography kit

Further, FIG. 3 shows the relationship between the detection sensitivity and L/BG in Examples 1 to 20 and Comparative Examples 1 to 3. If the value of L/BG is higher than the certain value, the detection sensitivity is decreased. It is because the time for detection of line without antigen is decreased, and as result the amplification time is decreased. Therefore, the present invention is characterized in that the ratio of the number of non-specifically adsorbed labeling substance in the detection site (L) and the non-detention site (BG) on the porous carrier is 0.4 to 2.5, preferably 0.7 to 2.0, and more preferably 0.8 to 1.5.

TABLE 1

|  | Example 1 | Example 2 | Example 3 | Comparative Example 1 | Comparative Example 2 | Comparative Example 3 |
|---|---|---|---|---|---|---|
| Antibody density (µg/mm2) | 0.11 | 0.005 | 1.4 | 0.004 | 1.4 | 1.4 |
| Gold colloid size (nm) | 50 | 100 | 15 | 100 | 100 | 15 |
| Material of membrane | Nitrocellulose | Nitrocellulose | Nitrocellulose | Nitrocellulose | Nitrocellulose | Nitrocellulose |
| Antibody for gold colloid | F(ab')2 | Not treated | F(ab')2 | Not treated | Not treated | Not treated |
| Antibody for membrane | Not treated | F(ab')2 | Not treated | Not treated | Not treated | Not treated |
| line portion non-specifically adsorbed gold density (L) (/mm2) | 3.0E+04 | 8.0E+03 | 9.0E+05 | 5.5E+03 | 6.0E+04 | 1.1E+06 |
| Non-line portion non-specifically adsorbed gold density (BG) (/mm2) | 2.7E+04 | 2.1E+04 | 3.6E+05 | 1.8E+04 | 2.3E+04 | 4.0E+05 |
| L/BG | 1.1 | 0.4 | 2.5 | 0.3 | 2.6 | 2.7 |
| False positive | none | none | none | none | present | none |
| Detection sensitivity (*) | 100 | 50 | 50 | 10 | — | 1 |

(*) Relative value when the value of Example 1 was defined as 100.

TABLE 2

|  | Example 4 | Example 5 | Example 6 |
|---|---|---|---|
| Antibody density (µg/mm2) | 0.02 | 0.02 | 0.02 |
| Gold colloid size (nm) | 50 | 50 | 50 |
| Material of membrane | Nitrocellulose | Nitrocellulose | Nitrocellulose |
| Antibody for gold colloid | F(ab')2 | F(ab')2 | Not treated |
| Antibody for membrane | Not treated | F(ab')2 | F(ab')2 |
| line portion non-specifically adsorbed gold density (L) (/mm2) | 2.4E+04 | 1.4E+04 | 1.8E+04 |
| Non-line portion non-specifically adsorbed gold density (BG) (/mm2) | 2.6E+04 | 2.3E+04 | 2.6E+04 |
| L/BG | 0.9 | 0.6 | 0.7 |
| False positive | none | none | none |
| Detection sensitivity (*) | 90 | 80 | 75 |

(*) Relative value when the value of Example 1 was defined as 100.

TABLE 3

|  | Example 7 | Example 8 | Example 9 | Example 10 |
|---|---|---|---|---|
| Antibody density (µg/mm2) | 0.007 | 0.007 | 0.007 | 0.007 |
| Gold colloid size (nm) | 20 | 80 | 15 | 100 |
| Material of membrane | Nitrocellulose | Nitrocellulose | Nitrocellulose | Nitrocellulose |
| Antibody for gold colloid | F(ab')2 | F(ab')2 | F(ab')2 | F(ab')2 |
| Antibody for membrane | F(ab')2 | F(ab')2 | F(ab')2 | F(ab')2 |
| line portion non-specifically adsorbed gold density (L) (/mm2) | 6.4E+04 | 1.6E+04 | 7.6E+04 | 9.0E+03 |
| Non-line portion non-specifically adsorbed gold density (BG) (/mm2) | 3.2E+04 | 2.2E+04 | 3.6E+04 | 1.5E+04 |
| L/BG | 2.0 | 0.7 | 2.1 | 0.6 |
| False positive | none | none | none | none |
| Detection sensitivity (*) | 85 | 80 | 70 | 60 |

(*) Relative value when the value of Example 1 was defined as 100.

TABLE 4

|  | Example 11 | Example 12 | Example 13 | Example 14 | Example 15 | Example 16 | Example 17 | Example 18 |
|---|---|---|---|---|---|---|---|---|
| Antibody density (μg/mm2) | 0.006 | 0.007 | 0.014 | 0.021 | 0.63 | 0.84 | 1.1 | 1.2 |
| Gold colloid size (nm) | 50 | 50 | 50 | 50 | 50 | 50 | 50 | 50 |
| Material of membrane | Nitro-Cellulose | Nitro-cellulose | Nitro-cellulose | Nitro-cellulose | Nitro-cellulose | Nitro-cellulose | Nitro-cellulose | Nitro-cellulose |
| Antibody for gold colloid | F(ab')2 | F(ab')2 | F(ab')2 | F(ab')2 | F(ab')2 | F(ab')2 | F(ab')2 | F(ab')2 |
| Antibody for membrane | Not treated | Not treated | Not treated | Not treated | Not treated | Not treated | Not treated | Not treated |
| Line portion non-specifically adsorbed gold density (L) (/mm2) | 1.5E+04 | 1.8E+04 | 1.9E+04 | 2.7E+04 | 3.6E+04 | 4.1E+04 | 5.6E+04 | 6.0E+04 |
| Non-line portion non-specifically adsorbed gold density (BG) (/mm2) | 2.5E+04 | 2.6E+04 | 2.4E+04 | 3.0E+04 | 2.6E+04 | 2.7E+04 | 2.8E+04 | 2.7E+04 |
| L/BG | 0.6 | 0.7 | 0.8 | 0.9 | 1.4 | 1.5 | 2.0 | 2.2 |
| False positive | none | none | none | none | none | none | none | none |
| Detection sensitivity (*) | 65 | 80 | 90 | 95 | 95 | 90 | 80 | 60 |

(*) Relative value when the value of Example 1 was defined as 100.

TABLE 5

|  | Example 1 | Example 19 | Example 20 |
|---|---|---|---|
| Antibody density (μg/mm2) | 0.11 | 0.11 | 0.11 |
| Gold colloid size (nm) | 50 | 50 | 50 |
| Material of membrane | Nitrocellulose | Polyethylene | Nylon |
| Antibody for gold colloid | F(ab')2 | F(ab')2 | F(ab')2 |
| Antibody for membrane | Not treated | Not treated | Not treated |
| line portion non-specifically adsorbed gold density (L) (/mm2) | 3.0E+04 | 3.5E+04 | 8.8E+04 |
| Non-line portion non-specifically adsorbed gold density (BG) (/mm2) | 2.7E+04 | 2.3E+04 | 3.6E+04 |
| L/BG | 1.1 | 1.5 | 2.4 |
| False positive | none | none | none |
| Detection sensitivity (*) | 100 | 90 | 70 |

(*) Relative value when the value of Example 1 was defined as 100.

The invention claimed is:

1. An immunochromatography method comprising, developing an analyte and a labeling substance which is modified with a first binding substance against the analyte in a mixed state on a porous carrier, wherein the porous carrier comprises a detection site and a non-detection site,
capturing the analyte and the labeling substance at the detection site on the porous carrier having a second binding substance against the analyte or a substance capable of binding to the first binding substance against the analyte, wherein the labeling substance is non-specifically adsorbed on the porous carrier at both the detection site and the non-detection site, and
performing amplification by adding an amplification solution containing a compound comprising silver and a reducing agent for silver ions, so as to detect the analyte, wherein a fragmented antibody is used as at least one of the binding substances, a density of the non-specifically adsorbed labeling substance is $10^6/mm^2$ or less; and a ratio of the number of the non-specifically adsorbed labeling substance in the detection site and that in the non-detection site of the porous carrier is between 0.4 to 2.5 before amplification.

2. The immunochromatography method according to claim 1, wherein a fragmented antibody is used as the first binding substance; a density of the second binding substance at the detection site is 0.007 μg/mm² to 1.1 μg/mm², and the labeling substance has a particle diameter of 20 nm to 80 nm.

3. The immunochromatography method according to claim 1, wherein the first binding substance is an antibody, and/or the second binding substance is an antibody.

4. The immunochromatography method according to claim 1, wherein a fragmented antibody which is an Fab fragment and/or F(ab')$_2$ fragment and/or Fab' fragment is used as the first binding substance.

5. The immunochromatography method according to claim 1, wherein the porous carrier is nitrocellulose or polyethylene.

* * * * *